United States Patent

[19]

Rivó et al.

[11] Patent Number: 5,912,245

[45] Date of Patent: Jun. 15, 1999

[54] ACID AMIDE DERIVATIVES AND PROCESS FOR THE PREPARATION THEREOF

[75] Inventors: Endre Rivó; Szilveszter E. Vizi; Gábor Makara; József Reiter; Gábor Blaskó; Gyula Simig; Lászlo Gaál; Márton Fekete, all of Budapest, Hungary

[73] Assignee: Egis Gyogyszergyar RT., Budapest, Hungary

[21] Appl. No.: 08/737,273

[22] PCT Filed: May 15, 1995

[86] PCT No.: PCT/HU95/00015

§ 371 Date: Feb. 14, 1997

§ 102(e) Date: Feb. 14, 1997

[87] PCT Pub. No.: WO95/31443

PCT Pub. Date: Nov. 23, 1995

[30] Foreign Application Priority Data

May 18, 1994 [HU] Hungary ................... 94 01522

[51] Int. Cl.⁶ .................... A61K 31/495; A61K 31/535; C07D 241/44; C07D 401/12

[52] U.S. Cl. .................... 514/249; 514/234.8; 544/119; 544/354

[58] Field of Search .................. 544/354, 119; 514/249, 234.8

[56] References Cited

U.S. PATENT DOCUMENTS 5,514,680 5/1996 Weber et al. ............... 514/249
5,750,525 5/1998 Huth et al. ................ 544/354

FOREIGN PATENT DOCUMENTS

94/00124 1/1994 WIPO .

OTHER PUBLICATIONS

Mohamed, *Al–Azhar Bull. Sci.* vol. 2 pp. 1–12 1991.
Zahran et al, *Al–Azhar Bull. Sci.*, vol. 5, pp. 821–834 Dec. 1994.
Drug Evaluations by the American Medical Association, pp. 765, 768–769 1993.
Doble, *Therapie 50*, pp. 319–337 1995.
Lees, *Pharmacology and Pathophysical 5*, pp. 51–74 1996.

*Primary Examiner*—Emily Bernhardt
*Attorney, Agent, or Firm*—Birch, Stewart, Kolasch & Birch, LLP

[57] ABSTRACT

The present invention is directed to an acid amide of the formula

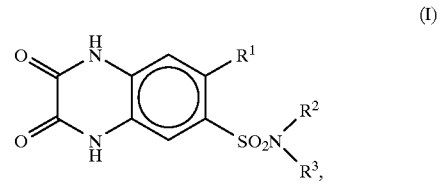

(I)

wherein
$R^1$ represents hydrogen or nitro,
$R^2$ and $R^3$ stand for, independently from each other, hydrogen, lower alkyl or lower alkenyl each optionally carrying a substituent selected from the group consisting of halogen, hydroxy, lower alkoxy, di(lower alkyl)amino, phenyl-lower alkoxycarbonyl and a 5- to 6-membered saturated hetero-ring selected from the group consisting of piperidino, pyrrolidino, piperazino and morpholino; or
$R^2$ and $R^3$ form, together with the adjacent nitrogen atom, a 6-membered saturated heterocyclic group selected from the group consisting of piperidino, pyrrolidino, piperazino and morpholino, said heterocyclic group optionally carrying a hydroxy or a hydroxy-lower alkyl group; or a
pharmaceutically acceptable salt thereof; process of making and pharmaceutical compositions and methods of treating.

15 Claims, No Drawings

ACID AMIDE DERIVATIVES AND PROCESS FOR THE PREPARATION THEREOF

This invention relates to new acid amides, a process for the preparation thereof, pharmaceutical compositions comprising the same, the use of the said compounds for the treatment of diseases and for the preparation of pharmaceutical compositions suitable for the treatment of diseases.

According to an aspect of the present invention there are provided new acid amides of the formula

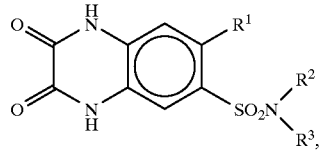

(I)

wherein $R^1$ represents hydrogen or nitro, $R^2$ and $R^3$ stand, independently from each other, for hydrogen, lower alkyl or lower alkenyl optionally carrying a substituent selected from the group consisting of halogen, hydroxy, lower alkoxy, di(lower alkyl) amino, phenyl-lower alkoxycarbonyl and a 5- to 6-membered saturated heteroring containing 1 or 2 nitrogen and/or oxygen atom(s); or $R^2$ and $R^3$ form, together with the adjacent nitrogen atom, a 6-membered saturated heterocyclic group containing optionally 1 or 2 additional nitrogen atoms and/or oxygen atom(s), said ring optionally carrying a hydroxy or a hydroxy-lower alkyl group.

The invention encompasses all of the possible mesomers, tautomeric forms and stereoisomers of the acid amides of the formula (I) and the mixtures thereof.

The compounds of the formula (I) are AMPA and kainate antagonists.

The term "lower" in respect of the alkyl and alkenyl groups means 1–6 and 2–6 carbon atoms, respectively.

The term "alkyl" used throughout the specification and claims refers to straight or branched ones such as methyl, ethyl, n-propyl, i-propyl, n-butyl, tert-butyl, n-hexyl etc. Suitably "alkenyl" may include straight or branched ones such as vinyl, allyl, methallyl, butenyl or the like. The term "halogen atom" encompasses all the four halogen atoms, such as fluorine, chlorine, bromine and iodine. As "5- to 6-membered heterorings" saturated heterocyclic rings are mentioned, which contain as heteroatom 1 or 2 nitrogen and/or oxygen atom(s) (e.g. pyrrolidinyl, piperidinyl, piperazinyl, pyrazolidinyl, imidazolidinyl, izoxazolidinyl, oxazolidinyl, hexahydropyridazinyl, hexahydropyrimidinyl, tetrahydro-2H-1,3-oxazinyl, tetrahydro-1H-1,2-oxazinyl or morpholinyl).

Preferred representatives of the compounds according to the invention are the following derivatives: 1,2,3,4-tetrahydro-7-nitro-2,3-dioxo-N-(2-piperidinoethyl)-6-quinoxaline sulfonamide, N,N-bis(2-hydroxyethyl)-1,2,3,4-tetrahydro-7-nitro-2,3-dioxo-6-quinoxaline sulfonamide and pharmaceutically acceptable salts thereof.

Those compounds of the formula (I), wherein $R^2$ and $R^3$ stand for basic groups, can form acid addition salts with pharmaceutically acceptable acids (e.g. hydrogen halides, sulfuric acid, maleic acid, fumaric acid, citric acid). From those compounds of the formula (I), wherein $R^2$ and $R^3$ represent hydrogen or alkyl, salts can be formed with mineral bases (such as sodium or potassium hydroxide), whereby the acid amides are converted into salts in form of lactimes.

According to a further aspect of the present invention there is provided a process for the preparation of acid amides of the formula (I), which comprises reacting an acid chloride of the formula

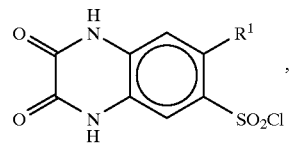

(II)

wherein $R^1$ is as stated above, with an amine of the formula

(III)

wherein $R^2$ and $R^3$ are as stated above, and optionally converting the thus-obtained compound of the formula (I) into a pharmaceutically acceptable salt.

The reaction of the acid chlorides of the formula (II) with the amines of the formula (III) is carried out in a polar solvent, preferably water or ethanol, at a temperature between −10° C. and +100° C., preferably at room temperature. The reaction time varies between 1 hour and 72 hours, preferably between 3 and 8 hours.

The product can be isolated from the reaction mixture by a method known per se. If the product separates from the reaction mixture in crystalline form, the crystals are filtered off. If the product does not separate from the reaction mixture as a consequence of the amine of the formula (III) applied in excess, the amine is bound with a mineral or organic acid (e.g. hydrogen chloride or acetic acid) added to the reaction mixture in excess, and then the separated product is filtered off. The product can be purified by recrystallization from an appropriate solvent or by precipitation from a solution formed with a solvent in which the given compound is readily soluble.

If the salt formation is carried out with a mineral or organic acid, the compound of the formula (I) is dissolved in an appropriate solvent (e.g. dimethylformamide or dimethyl sulfoxide), and then the desired acid is added to the solution. In those cases wherein a mineral acid has been used for the working up of the reaction mixture, the product separates directly in the form of an acid addition salt.

If the salt formation is carried out with a mineral base, the compound of the formula (I) is dissolved e.g. in a diluted (5–10%) warm solution of sodium or potassium hydroxide, the obtained solution is cooled and the separated salt is filtered off.

The acid chloride of the formula (II), wherein $R^1$ stands for hydrogen, is known from the literature [Japanese patent specification No. 26,975; Chem. Abstr. 62, 11833 (1965)].

The acid chloride of the formula (II), wherein $R^1$ stands for nitro, is a new compound. It can be prepared by nitrating an acid chloride of the formula (II), wherein $R^1$ represents hydrogen.

The compounds of the formula (III) are known from the literature. They are either commercially available or can be prepared by known methods [Houber-Weyl: "Methoden der Organischen Chemie", 9th band].

The compounds according to the invention possess valuable AMPA (α-amino-3-hydroxy-5-methyl-4-isoxazole propionic acid) and kainate antagonizing properties.

Among the known quinoxaline dione derivatives CNQX (6-cyano-7-nitro-quinoxaline-2,3-dione) and DNQX (6,7-dinitro-quinoxaline-2,3-dione) exhibit selective AMPA antagonizing property [M. J. Sheardown, E. O. Nielsen, A. J. Hansen, P. Jacobsen, T. Honoré: Science 247, 571–574, (1990)]. The NMDA (N-methyl-D-aspartate) antagonizing effect of the said compounds is 5 to 30 times weaker than the AMPA antagonizing property thereof [D. E. Murphy, E. W. Snowhill, M. Williams: Neurochem. Res. Vol. 12., 775–782 (1987)]. The AMPA antagonizing activity is useful in the medicinal prophylaxis of tissue injuries caused by epilepsy, lesions and internal haemorrhages [S. D. Donovan, M. A. Rogawski: Neuron Vol. 10, 51–59 (1993)]. The compounds having NMDA antagonizing effect can be useful in the therapy due to their anticonvulsive, muscle relaxant and antipsychotic properties. Furthermore they can influence to advantage the neurodegenerative processes developing for various reasons [J. Lehmann: Drugs of the Future, Vol. 14, 1059–1071 (1989)]. The compounds according to the invention are both AMPA and NMDA antagonists, so in the course of a therapeutic application they will probably be useful in a wider indication.

The activity of the compounds according to the invention is proved by the following tests. As reference the following compounds were applied:

DNQX=6,7-dinitroquinoxaline-2,3-dione

AMPA=α-amino-3-hydroxy-5-methyl-4-isoxazole propionic acid

MK-801=(+)-5-methyl-10,11-dihydro-5H-dibenzo [a,d] cyclohepten-5,10-imine[1]

[1] (M. Negwer: "Organic Chemical Drugs and their Synonymes", compound No. 3906)

CGS-19755=cis-4-phosphonomethylpiperidine-2-carboxylic acid[2].

[2] (EP patent No. 0,203,891)

1. $^3$H-AMPA and $^3$H-kainate binding (radioligand competitive binding assay)

The experiment was carried out according to the method of Murphy et al. [D. E. Murphy, E. W. Snowhill, M. Williams: Neurochem. Res. 12, 775–782 (1987)] using a membrane specimen isolated from rat brain. The binding of kainate labeled with tritium on a rat cortex specimen was measured according to the method of Honoré et al. [T. Honoré, J. Dejer and M. Nielsen: Neurosci. Lett. 65, 48–52 (1986)]. The inhibition constants ($K_i$) are shown in Table I.

TABLE I

| Compound (No. of Example) | Binding of 3H-AMPA $K_i$ (Mole) | Binding of $^3$H-kainate $K_i$ (Mole) |
|---|---|---|
| 17 | $6.3 \cdot 10^{-7}$ | $2.0 \cdot 10^{-6}$ |
| 11 | $1.4 \cdot 10^{-6}$ | $3.2 \cdot 10^{-6}$ |
| 12 | $2.0 \cdot 10^{-5}$ | $1.0 \cdot 10^{-3}$ |
| 24 | $2.1 \cdot 10^{-6}$ | $2.4 \cdot 10^{-5}$ |
| 23 | $8.6 \cdot 10^{-6}$ | $4.2 \cdot 10^{-4}$ |
| 13 | $1.0 \cdot 10^{-5}$ | $6.7 \cdot 10^{-6}$ |
| 19 | $4.4 \cdot 10^{-6}$ | $3.8 \cdot 10^{-6}$ |
| 14 | $1.6 \cdot 10^{-6}$ | $1.5 \cdot 10^{-5}$ |
| 26 | $1.6 \cdot 10^{-6}$ | $1.7 \cdot 10^{-3}$ |
| 16 | $1.3 \cdot 10^{-5}$ | $1.6 \cdot 10^{-5}$ |
| 15 | $8.2 \cdot 10^{-6}$ | $1.5 \cdot 10^{-5}$ |
| DNQX | $8.8 \cdot 10^{-7}$ | $2.0 \cdot 10^{-6}$ |
| AMPA | $1.4 \cdot 10^{-8}$ | — |
| Kainate | — | $2.2 \cdot 10^{-8}$ |

From the data of the above Table I it can be established that the most active compound, the compound of Example 17, displaced labeled kainate and AMPA with an affinity similar to that of DNQX. Thus, the said molecule is a good reversible ligand for both the AMPA and kainate recognition site.

2. Selectivity

The experiment was carried out according to the method of Foster et al. [A. Foster and E. H. F. Wong: Brit. J. Pharmacol. 91, 403–409, (1987)]. When applying the CGS 19755 receptor binding test the method of Murphy et al. [D. E. Murphy, A. J. Hutchison, S. D. Hurt, M. Williams and M. A. Sills: Brit. J. Pharmacol. 95, 932–938 (1988)] was applied. The data are shown in Table II.

TABLE II

| Compound (No. of Example) | Binding of $^3$H-MK-801 $K_i$ (Mole/l) | Binding of $^3$H-CGS-19755 $K_i$ (Mole/l) |
|---|---|---|
| 17 | $3.9 \cdot 10^{-3}$ | non-linear regression does not "converge" |
| 24 | $2.8 \cdot 10^{-3}$ | non-linear regression does not "converge" |
| DNQX | $8.9 \cdot 10^{-6}$ | non-linear regression does not "converge" |

From the above Table II it can be established that the examined compounds are weak displacers of MK-801, but failed to displace at all the reversible NMDA antagonist tracer CGS-19755. Therefore the compounds of Examples 17 and 24 are selective AMPA and kainate antagonists, and as it is to be expected, they will be useful in the treatment of diseases connected with glutamatergic neurontransmission (ischemia, cerebral and spinal injuries, hypoglycemia, chronic neurodegenerative diseases).

According to a further aspect of the present invention there are provided pharmaceutical compositions comprising as active ingredient a compound of the formula (I) or a pharmaceutically acceptable salt thereof in admixture with suitable inert solid or liquid pharmaceutical carriers.

The pharmaceutical compositions of the present invention can be prepared by methods known per se by admixing the active ingredient with suitable inert, non-toxic, solid or liquid carriers and bringing the mixture to galenic form.

It is preferred to finish the compounds of the formula (I) to tablets or dragées, but they can be administered in form of solution or suspension, too. The daily oral dose is generally 10 to 1000 mg, preferably 100 to 600 mg for an adult human being of about 70 kg.

According to a further aspect of the present invention there is provided the use of the compounds of the formula (I) or pharmaceutically acceptable salts thereof for the preparation of pharmaceutical compositions having particularly AMPA and kainate antagonizing properties.

According to a still further aspect of the present invention there is provided a method of AMPA and kainate antagonizing treatment, which comprises administering to a patient an effective amount of a compound of the formula (I) or a pharmaceutically acceptable salt thereof.

Further details of the present invention are to be found in the following Examples without limiting the scope of protection to the said Examples.

EXAMPLE 1

1,2,3,4-Tetrahydro-2,3-dioxo-6-quinoxaline sulfonamide and its disodium salt

A suspension of 5.21 g (0.02 mole) of 1,2,3,4-tetrahydro-2,3-dioxo-6-quinoxalinesulfonyl chloride and 40 ml of 25% ammonium hydroxide is stirred at room temperature for 6 hours. Then it is filtered, the separated material is washed with water and acetone, filtered, dried, dissolved in a slight amount of hot dimethyl sulfoxide, and the product is precipitated from the solution by adding a slight amount of 2-propanol to it. Thus 0.70 g (15%) of 1,2,3,4-tetrahydro-2,3-dioxo-6-quinoxaline sulfonamide is obtained, m.p.: >360° C.

0.70 g of the above compound are dissolved in 10 ml of a hot 10% aqueous sodium hydroxide solution. On cooling the desired disodium salt separates, m.p. is higher than 350° C.

EXAMPLE 2

N,N-Dimethyl-1,2,3,4-tetrahydro-2,3-dioxo-6-quinoxaline sulfonamide

A mixture of 3.91 g (0.015 mole) of 1,2,3,4-tetrahydro-2,3-dioxo-6-quinoxalinesulfonyl chloride and 30 ml of 25% aqueous dimethylamine is stirred at room temperature for 6 hours. Then it is filtered, the separated crystals are washed successively with water and acetone, filtered, dried and recrystallized from water. Thus 1.40 g (35%) of N,N-dimethyl-1,2,3,4-tetrahydro-2,3-dioxo-6-quinoxaline sulfonamide is obtained, m.p.: 258–266° C.

EXAMPLE 3

N-(2-Bromoethyl)-1,2,3,4-tetrahydro-2,3-dioxo-6-quinoxaline sulfonamide 20.49 g (0.1 mole) of 2-bromoethylamine hydrobromide and 4.00 g (0.1 mole) of sodium hydroxide are dissolved in 60 ml of water, and 7.82 g (0.03 mole) of 1,2,3,4-tetrahydro-2,3-dioxo-6-quinoxalinesulfonyl chloride are added to the solution, and the mixture is stirred at room temperature for 6 hours. Then it is allowed to stand for 16 hours. The separated crystals are filtered, washed successively with water and acetone, dried, dissolved in a slight amount of hot dimethyl sulfoxide and precipitated from the solution with water. Thus 3.44 g (33%) of N-(2-bromoethyl)-1,2,3,4-tetrahydro-2,3-dioxo-6-quinoxaline sulfonamide are obtained, m.p.: 261–266° C.

EXAMPLE 4

N,N-bis- (2-hydroxyethyl)-1,2,3,4-tetrahydro-2,3-dioxo-6-quinoxaline sulfonamide To a solution of 10.51 g (0.1 mole) of diethanolamine in 40 ml of water 5.21 g (0.02 mole) of 1,2,3,4-tetrahydro-2,3-dioxo-6-quinoxalinesulfonyl chloride are added in small portions, under stirring. The mixture is stirred at room temperature for 10 hours and allowed to stand for 16 hours. The separated crystals are filtered, washed successively with water and acetone, dried, dissolved in a slight amount of hot dimethyl sulfoxide and precipitated from the solution with water. Thus 3.37 g (51%) of N.N-bis-(2-hydroxyethyl)-1,2,3,4-tetrahydro-2,3-dioxo-6-quinoxaline sulfonamide are obtained, m.p.: 272–276° C.

According to the method of Example 4 the following acid amides were prepared:

EXAMPLE 5

1-(1,2,3,4-Tetrahydro-2,3-dioxo-6-quinoxalinesulfonyl)piperidine M.p.: >335° C. Yield: 79%.

EXAMPLE 6

4-(1,2,3,4-Tetrahydro-2,3-dioxo-6-quinoxalinesulfonyl)-morpholine

M.p.: >330° C. Yield: 66%.

EXAMPLE 7

N-(Benzyloxycarbonylmethyl)-1,2,3,4-tetrahydro-2,3-dioxo-6-quinoxaline sulfonamide To a solution of 4.14 g (0.03 mole) of potassium carbonate in 25 ml of water 10.12 g (0.03 mole) of aminoacetic acid benzyl ester tosylate are added in small portions, under stirring. Then 5.21 g (0.02 mole) of 1,2,3,4-tetrahydro-2,3-dioxo-6-quinoxalinesulfonyl chloride are added to the mixture, it is stirred at room temperature for 6 hours and allowed to stand for 16 hours. The separated crystals are filtered off, washed with water and acetone, dried, dissolved in a slight amount of hot dimethyl sulfoxide and precipitated with water. Thus 3.50 g (45%) of N-(benzyloxycarbonylmethyl)-1,2,3,4-tetrahydro-2,3-dioxo-6-quinoxaline sulfonamide are obtained.

M.p.: 270–280° C.

EXAMPLE 8

N-(n-Butyl)-1,2,3,4-tetrahydro-2,3-dioxo-6-quinoxaline sulfonamide

To a solution of 7.31 g (0.1 mole) of n-butylamine in 20 ml of water 5.21 g (0.02 mole) of 1,2,3,4-tetrahydro-2,3-dioxo-6-quinoxalinesulfonyl chloride are added, and the mixture is stirred at room temperature for 5 hours. Then it is allowed to stand for 16 hours, the separated crystals are filtered off, washed with water, dried and recrystallized from acetone. Thus 4.50 g (76%) of N-(n-butyl)-1,2,3,4-tetrahydro-2,3-dioxo-6-quinoxaline sulfonamide are obtained, m.p.: 257–262° C.

EXAMPLE 9

1,2,3,4-Tetrahydro-N-(2-methoxyethyl)-2,3-dioxo-6-quinoxaline sulfonamide

To a solution of 7.51 g (0.1 mole) of 2-methoxyethylamine in 20 ml of water 5.21 g (0.02 mole) of 1,2,3,4-tetrahydro-2,3-dioxo-6-quinoxalinesulfonyl chloride are added in small portions, under stirring, and the mixture is stirred at room temperature for 16 hours. It is allowed to stand further for 2 days, and then 15 ml of acetic acid and 10 ml of water are added to it. The separated crystals are filtered, washed successively with water and acetone, dried, dissolved in a slight amount of hot dimethyl sulfoxide and precipitated from the solution with water. Thus 3.80 g (63%) of 1,2,3,4-tetra-hydro-N-(2-methoxyethyl)-2,3-dioxo-6-quinoxaline sulfonamide are obtained, m.p.: 264–267° C.

EXAMPLE 10

1,2,3,4-Tetrahydro-7-nitro-2,3-dioxo-6-quinoxaline sulfonamide

A mixture of 4.58 g (0.015 mole) of 1,2,3,4-tetrahydro-7-nitro-2,3-dioxo-6-quinoxalinesulfonyl chloride and 30 ml of 25% ammonium hydroxyde is stirred at a temperature between 5° C. and 10° C. for 3 hours and then allowed to stand for 16 hours. To the mixture 6 ml of acetic acid and 40 ml of water are added, the separated crystals are filtered off, washed with water and acetone, dried and dissolved in a slight amount of hot dimethyl sulfoxide. The product is precipitated from this solution with 2-propanol. Thus 1.40 g (17%) of 1,2,3,4-tetrahydro-7-nitro-2,3-dioxo-6-quinoxaline sulfonamide are obtained, m.p.: >330° C.

EXAMPLE 11

N,N-Dimethyl-1,2,3,4-tetrahydro-7-nitro-2,3-dioxo-6-quinoxaline sulfonamide

A mixture of 4.58 g (0.015 mole) of 1,2,3,4-tetrahydro-7-nitro-2,3-dioxo-6-quinoxalinesulfonyl chloride and 30 ml of 25% ethanolic dimethylamine is stirred at a temperature between 5° C. and 10° C. for 3 hours, and then allowed to stand for 16 hours. To the reaction mixture 5 ml of acetic acid and 60 ml of water are added, the separated crystals are filtered, washed with water and acetone, dried, dissolved in a slight amount of hot dimethyl sulfoxide and precipitated from this solution with water. Thus 3.80 g (81%) of N,N-dimethyl-1,2,3,4-tetrahydro-7-nitro-2,3-dioxo-6-quinoxaline sulfonamide are obtained, m.p.: 318–332° C.

EXAMPLE 12

N,N-Diethyl-1,2,3,4-tetrahydro-7-nitro-2,3-dioxo-6-quinoxaline sulfonamide

To a solution of 10.97 g (0.015 mole) of diethylamine in 20 ml of acetone 4.58 g (0.015 mole) of 1,2,3,4-tetrahydro-7-nitro-2,3-dioxo-6-quinoxalinesulfonyl chloride are added a temperature between 5° C. and 10° C., under stirring, the mixture is stirred at the same temperature for 3 hours and allowed to stand for 16 hours. Then 6 ml of acetic acid and 40 ml of water are added to the mixture, the separated crystals are filtered off, washed with water and acetone, dried and recrystallized from acetonitrile. Thus 3.50 g (59%) of N,N-diethyl-1,2,3,4-tetrahydro-7-nitro-2,3-dioxo-6-quinoxaline sulfonamide are obtained, m.p.: >360° C.

EXAMPLE 13

1,2,3,4-Tetrahydro-N-(2-methoxyethyl)-7-nitro-2,3-dioxo-6-quinoxaline sulfonamide To a solution of 3.76 g (0.05 mole) of 2-methoxyethylamine in 15 ml of water 6.11 g (0.02 mole) of 1,2,3,4-tetrahydro-7-nitro-2,3-dioxo-6-quinoxalinesulfonyl chloride are added at room temperature, under stirring. The mixture is stirred at room temperature for 6 hours and then allowed to stand for 16 hours. The separated crystals are filtered off, washed successively with water and acetone, filtered again, dried and dissolved in a slight amount of hot dimethyl sulfoxide. The product is precipitated from this solution with water. Thus 4.05 g (59%) of 1,2,3,4-tetrahydro-N-(2-methoxy-ethyl)-7-nitro-2,3-dioxo-6-quinoxaline sulfonamide are obtained, m.p.: 320–321° C.

According to the method of Example 13 the following acid amides of the formula (I) were prepared:

EXAMPLE 14

N-(3-Dimethylaminopropyl)-1,2,3,4-tetrahydro-7-nitro-2,3-dioxo-6-quinoxaline sulfonamide M.p.: 195–206° C. Yield: 84%.

In order to prepare the corresponding hydrochloride salt, the thus-obtained compound is dissolved in dimethyl formamide, a 10% solution of hydrochloric acid in isopropanol is added, the separated crystals are filtered off and washed with isopropanol. The melting point of the crystals is higher than 340° C.

EXAMPLE 15

1-(1,2,3,4-Tetrahydro-7-nitro-2,3-dioxo-6-quinoxaline-sulfonyl)-4-hydroxypiperidine M.p.: 310–315° C. Yield: 45%.

EXAMPLE 16

1-(2-Hydroxyethyl)-4-(1,2,3,4-tetrahydro-7-nitro-2,3-dioxo-6-quinoxalinesulfonyl)-piperazine M.p.: 273–275° C. Yield: 54%.

EXAMPLE 17

1,2,3,4-Tetrahydro-7-nitro-2,3-dioxo-N-(2-piperidinoethyl)-6-quinoxaline sulfonamide M.p.: 272–280° C. Yield: 82%.

EXAMPLE 18

N,N-Diallyl-1,2,3,4-tetrahydro-7-nitro-2,3-dioxo-6-quinoxaline sulfonamide

M.p.: >360° C. Yield: 90%.

EXAMPLE 19

N-Allyl-1,2,3,4-tetrahydro-7-nitro-2,3-dioxo-6-quinoxaline sulfonamide

M.p.: 260–265° C. Yield: 31%.

EXAMPLE 20

1,2,3,4-Tetrahydro-N-[3-(4-morpholino)-propyly]-7-nitro-2,3-dioxo-6-quinoxaline sulfonamide M.p.: 256–262° C. Yield: 17%.

EXAMPLE 21

1,2,3,4-Tetrahydro-N-[2-(4-morpholino)-ethyl]-7-nitro-2,3-dioxo-6-quinoxaline sulfonamide M.p.: 283–291° C. Yield: 18%.

EXAMPLE 22

1,2,3,4-Tetrahydro-N-[2-(1-pyrrolidinoethyl)]-7-nitro-2,3-dioxo-6-quinoxaline sulfonamide M.p.: 268–277° C. Yield: 56%.

EXAMPLE 23

N-(n-Butyl)-N-(2-hydroxyethyl)-1,2,3,4-tetrahydro-7-nitro-2,3-dioxo-6-quinoxaline sulfonamide M.p.: 295–3160° C. Yield: 15%.

EXAMPLE 24

N,N-bis(2-Hydroxyethyl)-1,2,3,4-tetrahydro-7-nitro-2,3-dioxo-6-quinoxaline sulfonamide To a solution of 10,5 g (0.1 mole) of diethanolamine in 40 ml of water 6.11 g (0.02 mole) of 1,2,3,4-tetrahydro-7-nitro-2,3-dioxo-6-quinoxalinesulfonyl chloride are added under stirring, the reaction mixture is stirred at room temperature for 6 hours and then allowed to stand for 16 hours. The separated crystals are filtered off, washed with water, dried and recrystallized from acetone. Thus 3.90 g (52%) of N,N-bis(2-hydroxyethyl)-1,2,3,4-tetrahydro-7-nitro-2,3-dioxo-6-quinoxaline sulfonamide are obtained, m.p.: 310–321° C.

EXAMPLE 25

1,2,3,4-Tetrahydro-N-(2-hydroxyethyl)-7-nitro-2,3-dioxo-6-quinoxaline sulfonamide To a solution of 6.11 g (0.1 mole) of ethanolamine in 40 ml of water 6.11 g (0.02 mole) of 1,2,3,4-tetrahydro-7-nitro-2,3-dioxo-6-quinoxalinesulfonyl chloride are added under stirring, the reaction mixture is stirred at room temperature for 6 hours and then allowed to stand for 16 hours. The separated crystals are filtered off, washed with acetone, dried, dissolved in a slight amount of hot dimethyl sulfoxide and precipitated from this solution with 2-propanol. Thus 3.70 g (56%) of 1,2,3,4-tetrahydro-N-(2-hydroxyethyl)-7-nitro-2,3-dioxo-6-quinoxaline sulfonamide are obtained, m.p.: 281–289° C.

EXAMPLE 26

1-(1,2,3,4-Tetrahydro-7-nitro-2,.3-dioxo,-6-quinoxaline-sulfonyl)-morpholine

To a solution of 8.72 g (0.1 mole) of morpholine in 80 ml of water 6.11 g (0.02 mole) of 1,2,3,4-tetrahydro-7-nitro-2, 3-dioxo-6-quinoxalinesulfonyl chloride are added under stirring, the reaction mixture is stirred at room temperature for 6 hours and then allowed to stand for 16 hours. The separated crystals are filtered off, washed with water, dried, dissolved in a slight amount of hot dimethyl sulfoxide and precipitated from this solution with water. Thus 5.76 g (81%) 1-(1,2,3,4-tetrahydro-7-nitro-2,3-dioxo-6-quinoxaline-sulfonyl)-morpholine are obtained, m.p.: >360° C.

What we claim is:

1. An acid amide of the formula

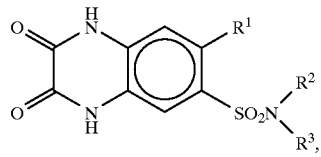

wherein
R$^1$ represents nitro,
R$^2$ and R$^3$ stand for, independently from each other, hydrogen, lower alkyl or lower alkenyl each optionally carrying a substituent selected from the group consisting of halogen, hydroxy, lower alkoxy, di(lower alkyl)amino, phenyl-lower alkoxycarbonyl and a 5- to 6-membered saturated heteroring selected from the group consisting of piperidino, pyrrolidino, piperazino and morpholino; or
R$^2$ and R$^3$ form, together with the adjacent nitrogen atom, a 6-membered saturated heterocyclic group selected from the group consisting of piperidino, pyrrolidino, piperazino and morpholino, said heterocyclic group optionally carrying a hydroxy or a hydroxy-lower alkyl group; or a pharmaceutically acceptable salt thereof.

2. 1,2,3,4-Tetrahydro-7-nitro-2,3-dioxo-N-(2-piperidino-ethyl)-6-quinoxaline sulfonamide, or a pharmaceutically acceptable salt thereof.

3. N,N-bis(2-hydroxyethyl)-1,2,3,4-tetrahydro-7-nitro-2, 3-dioxo-6-quinoxaline sulfonamide, or a pharmaceutically acceptable salt thereof.

4. A process for the preparation of an acid amide of the formula

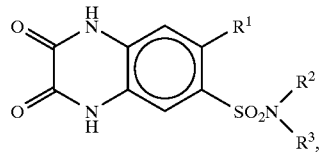

or a pharmaceutically acceptable salt thereof, which comprises reacting an acid chloride of the formula

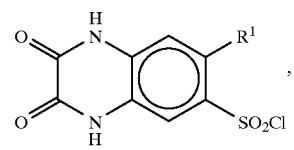

wherein R$^1$ represents nitro, with an amine of the formula

wherein
R$^2$ and R$^3$ stand for, independently from each other, hydrogen, lower alkyl or lower alkenyl each optionally carrying a substituent selected from the group consisting of halogen, hydroxy, lower alkoxy, di(lower alkyl)amino, phenyl-lower alkoxycarbonyl and a 5- to 6-membered saturated hetero-ring selected from the group consisting of piperidino, pyrrolidino, piperazino and morpholino; or
R$^2$ and R$^3$ form, together with the adjacent nitrogen atom, a 6-membered saturated heterocyclic group selected from the group consisting of piperidino, pyrrolidino, piperazino and morpholino, said heterocyclic group optionally carrying a hydroxy or a hydroxy-lower alkyl group and, if desired, converting the thus-obtained compound of the formula (I) into a pharmaceutically acceptable salt.

5. A process as claimed in claim 4, which comprises carrying out the reaction in a polar solvent.

6. A pharmaceutical composition comprising as active ingredient a therapeutically effective amount of a compound of the formula (I) according to claim 1, or a pharmaceutically acceptable salt thereof in admixture with a suitable inert solid or liquid pharmaceutical carrier.

7. A process for the preparation of pharmaceutical compositions according to claim 6, which comprises admixing a compound of the formula (I) or a pharmaceutically acceptable salt thereof with suitable inert solid or liquid therapeutical carriers.

8. The composition according to claim 6, wherein said compound is 1,2,3,4-Tetrahydro-7-nitro-2,3-dioxo-N-(2-piperidino-ethyl)-6-quinoxaline sulfonamide or a pharmaceutically acceptable salt thereof.

9. The composition according to claim 6, wherein said compound is N,N-bis(2-hydroxyethyl)-1,2,3,4-tetrahydro-7-nitro-2,3-dioxo-6-quinoxaline sulfonamide, or a pharmaceutically acceptable salt thereof.

10. A method of treating epilepsy which comprises administering to a patient in need of said treatment a therapeutically effective amount of a compound of the formula (I) according to claim 1, or a pharmaceutically acceptable salt thereof.

11. The method according to claim 10, wherein said compound is 1,2,3,4-Tetrahydro-7-nitro-2,3-dioxo-N-(2-piperidino-ethyl)-6-quinoxaline sulfonamide or a pharmaceutically acceptable salt thereof.

12. The method according to claim 10, wherein said compound is N,N-bis(2-hydroxyethyl)-1,2,3,4-tetrahydro-7-nitro-2,3-dioxo-6-quinoxaline sulfonamide, or a pharmaceutically acceptable salt thereof.

13. A method of relaxing muscles which comprises administering to a patient in need of said treatment a therapeutically effective amount of a compound of the formula (I) according to claim 1, or a pharmaceutically acceptable salt thereof.

14. The method according to claim 13, wherein said compound is 1,2,3,4-Tetrahydro-7-nitro-2,3-dioxo-N-(2-piperidino-ethyl)-6-quinoxaline sulfonamide or a pharmaceutically acceptable salt thereof.

15. The method according to claim 13, wherein said compound is N,N-bis(2-hydroxyethyl)-1,2,3,4-tetrahydro-7-nitro-2,3-dioxo-6-quinoxaline sulfonamide, or a pharmaceutically acceptable salt thereof.

\* \* \* \* \*